United States Patent
He

(10) Patent No.: US 9,428,384 B2
(45) Date of Patent: Aug. 30, 2016

(54) INSPECTION INSTRUMENT

(76) Inventor: Jizhong He, San Jose, CA (US)

(*) Notice: Subject to any disclaimer, the term of this patent is extended or adjusted under 35 U.S.C. 154(b) by 471 days.

(21) Appl. No.: 13/352,289

(22) Filed: Jan. 17, 2012

(65) Prior Publication Data

US 2012/0182412 A1    Jul. 19, 2012

Related U.S. Application Data

(60) Provisional application No. 61/433,758, filed on Jan. 18, 2011.

(51) Int. Cl.
| | |
|---|---|
| *G01N 21/01* | (2006.01) |
| *B82Y 35/00* | (2011.01) |
| *G01N 21/88* | (2006.01) |
| *G01Q 30/02* | (2010.01) |
| *G02B 21/00* | (2006.01) |
| *G01N 21/95* | (2006.01) |

(52) U.S. Cl.
CPC .............. *B82Y 35/00* (2013.01); *G01N 21/88* (2013.01); *G01Q 30/02* (2013.01); *G01Q 30/025* (2013.01); *G02B 21/0016* (2013.01); *G01N 21/9501* (2013.01); *G01N 2021/8825* (2013.01); *Y10T 29/49826* (2015.01)

(58) Field of Classification Search
CPC ...................... G01N 21/9501; G01N 21/8806; G01N 21/956; H01L 22/12; H01L 21/67288; G02B 21/12; G02B 21/14
USPC .................... 356/237.1, 237.2, 237.3, 237.5; 359/385, 368, 362
See application file for complete search history.

(56) References Cited

U.S. PATENT DOCUMENTS

| | | | | |
|---|---|---|---|---|
| 3,647,282 | A * | 3/1972 | Taira | 359/661 |
| 5,641,960 | A * | 6/1997 | Okubo | G01B 11/022 |
| | | | | 250/307 |
| 6,324,298 | B1 * | 11/2001 | O'Dell et al. | 382/149 |
| 2002/0015146 | A1 * | 2/2002 | Meeks et al. | 356/73 |
| 2005/0117204 | A1 * | 6/2005 | Kinoshita et al. | 359/368 |
| 2008/0013169 | A1 * | 1/2008 | Korpinen et al. | 359/385 |

OTHER PUBLICATIONS http://www.nikonmetrology.com/Products/Semiconductor-Systems/Semiconductor-Microscopes.*
http://machinedesign.com/archive/servomotors-stabilize-and-position-sensor-turrets-uavs.*
http://www.stigp.com/02_01turret_at268.htm.*

* cited by examiner

*Primary Examiner* — Tarifur Chowdhury
*Assistant Examiner* — Mohamed K Amara

(57) ABSTRACT

The present disclosure relates an inspection instrument adapted to increase testing throughput in a manufacturing process. In one embodiment, the inspection instrument includes a base plate and a vertical frame, where the base plate and the vertical frame are configured to provide structural support of the inspection instrument, a first mounting mechanism coupled to the base plate, where the first mounting mechanism is configured to hold a sample for inspection, and a second mounting mechanism coupled to the vertical frame, where the second mounting mechanism is configured to hold a set of sensors and an optical system for inspecting the sample. The first mounting mechanism and the second mounting mechanism are decoupled from each other to reduce impact of movements of the sample to the set of sensors and the optical system.

28 Claims, 6 Drawing Sheets

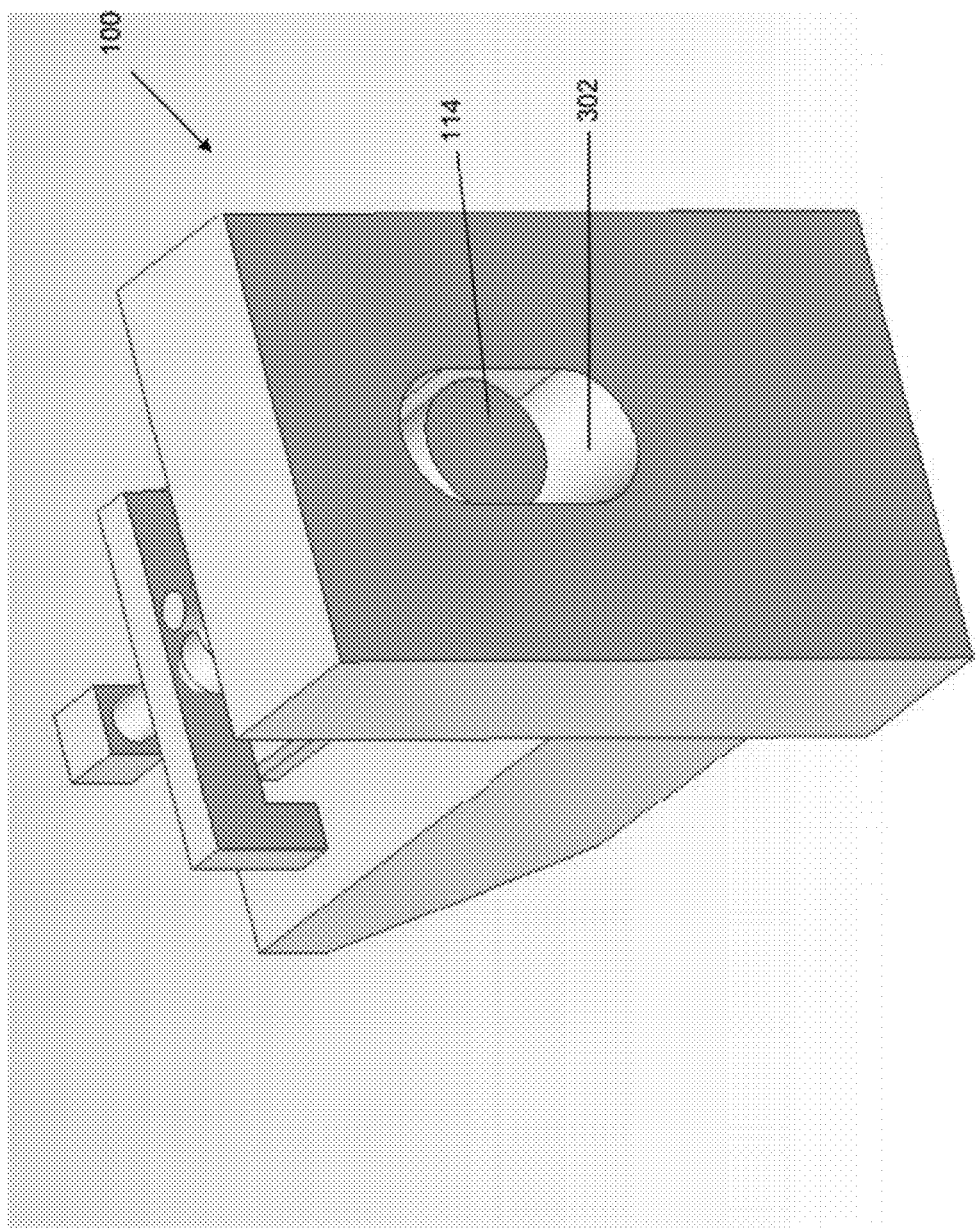

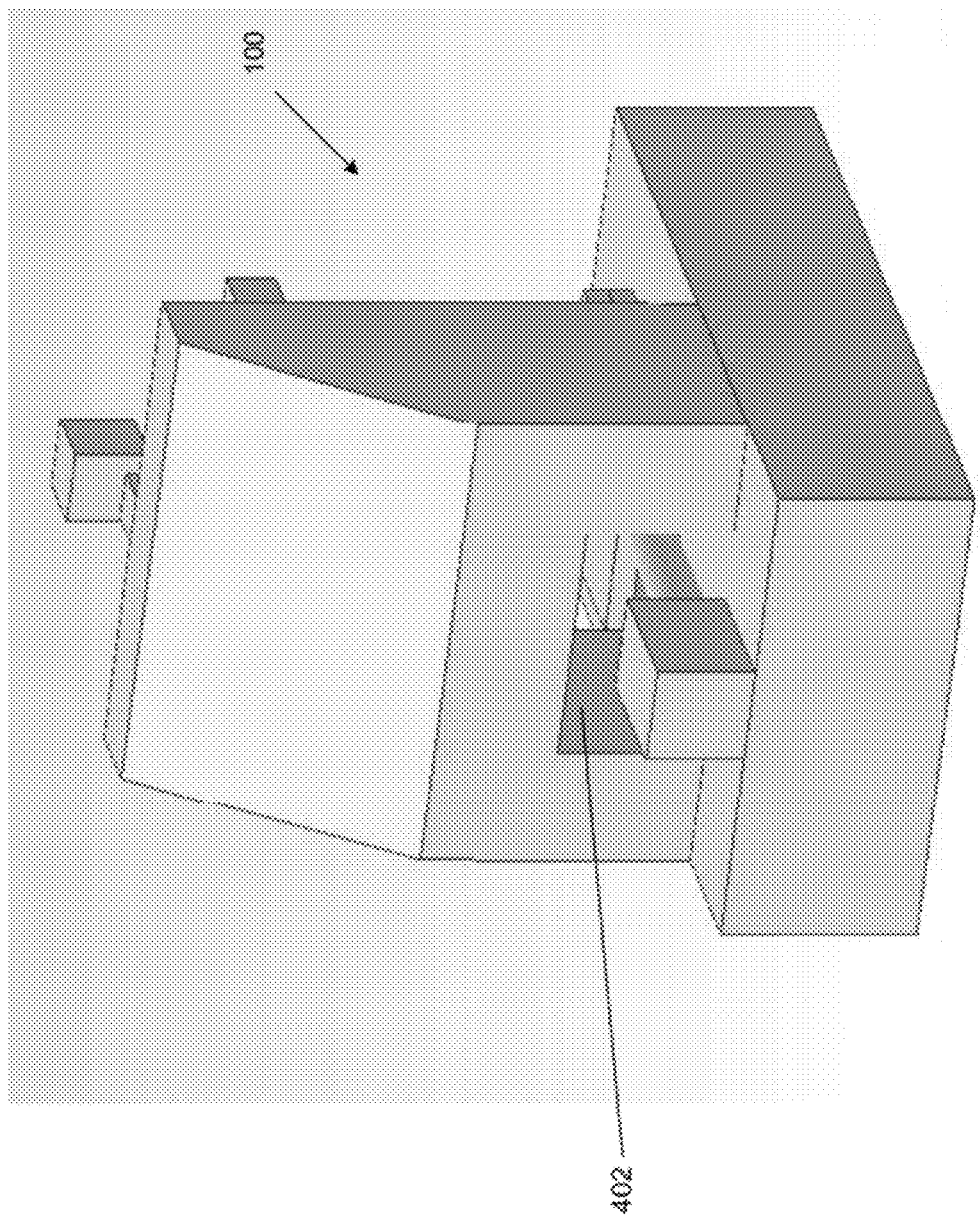

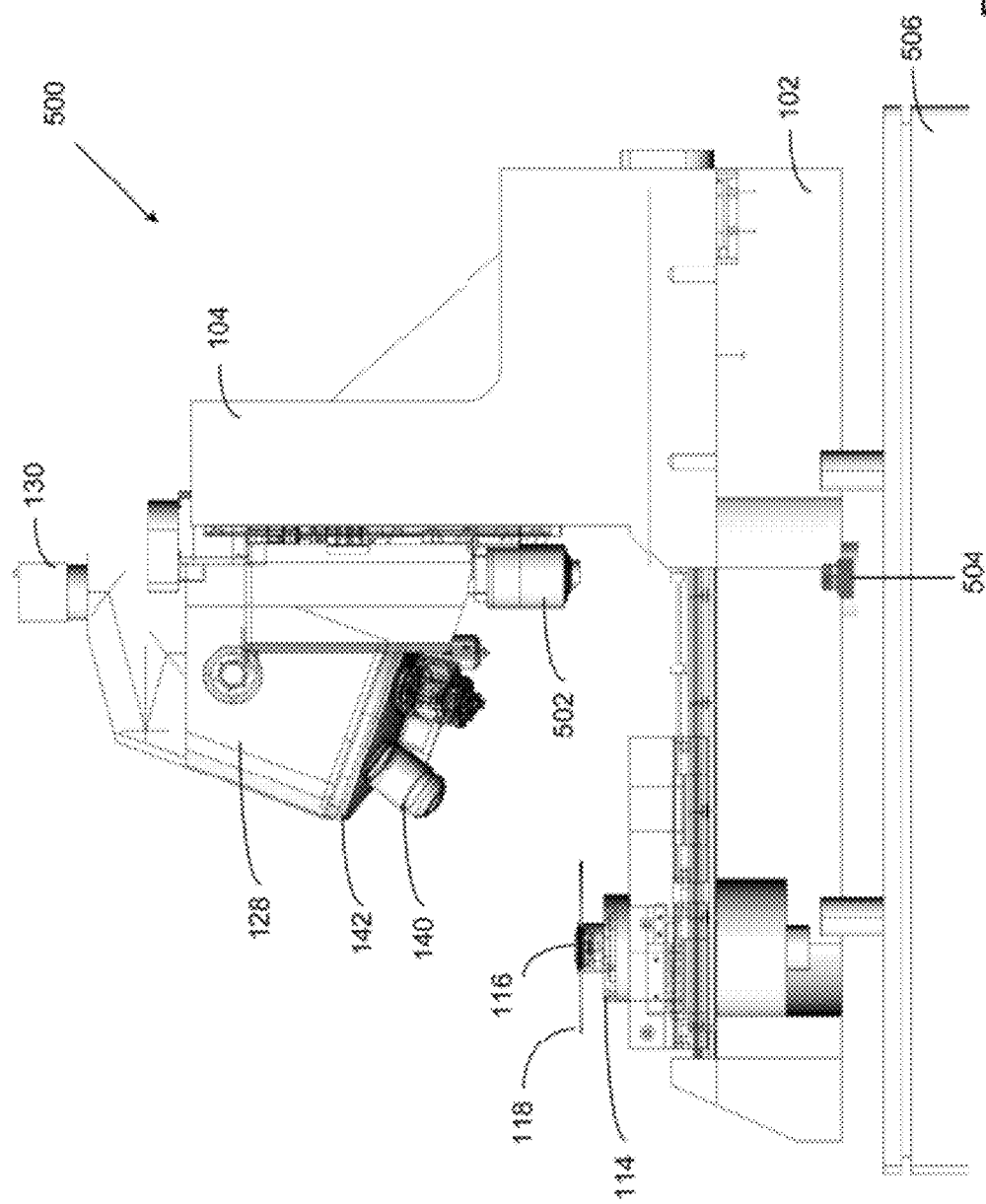

INSPECTION INSTRUMENT

CROSS REFERENCE TO RELATED APPLICATIONS

This application claims the benefit of U.S. provisional application No. 61/433,758, "An Inspection Instrument" filed Jan. 18, 2011. The aforementioned United States application is hereby incorporated by reference in its entirety.

FIELD

The present disclosure relates to the field of test and measurement instruments. In particular, the present disclosure relates to an inspection instrument adapted to increase testing throughput in a manufacturing process.

BACKGROUND

There are a number of challenges encountered in conventional scanning probe microscopy used in inspection of samples, such as integrated circuits and magnetic disks. First, different types of sensors are required to identify defects in a sample. After identifying certain defects, the sample may need to be relocated to another inspection instrument to further analyze other defects. The relocation of the sample would require additional time and effort to identify the original defects before further analysis may be performed. Second, in the conventional scanning probe microscopy, the structure that holds the sample and the structure that holds the sensors and optical system are integrated. As a result, movements and vibrations from the structure that holds the sample often introduce movements and vibrations to the structure that holds the sensors and optical systems. Thus, this problem causes degradation in quality of the inspection images of the sample. Third, in some of the conventional inspection instruments, stability of the conventional inspection instrument can be improved.

Therefore, there is a need for systems and methods that can address the above issues of the conventional inspection instruments.

SUMMARY

The present disclosure relates an inspection instrument adapted to increase testing throughput in a manufacturing process. In one embodiment, the inspection instrument includes a base plate and a vertical frame, where the base plate and the vertical frame are configured to provide structural support of the inspection instrument, a first mounting mechanism coupled to the base plate, where the first mounting mechanism is configured to hold a sample for inspection, and a second mounting mechanism coupled to the vertical frame, where the second mounting mechanism is configured to hold a set of sensors and an optical system for inspecting the sample. The first mounting mechanism and the second mounting mechanism are decoupled from each other to reduce impact of movements of the sample to the set of sensors and the optical system. The base plate includes a first opening configured to house at least a part of the first mounting mechanism. The first opening reduces center of gravity of the first mounting mechanism with respect to the base plate; and the first opening reduces distance between the second mounting mechanism and the vertical frame to improve stability of the inspection instrument. The vertical frame includes a second opening configured to provide a clearance to install a stage plate from back of the inspection instrument.

The first mounting mechanism includes a stage plate mounted to the base plate on a pair of base plate linear guides, and a stage servo motor configured to control the position of the base plate using a first ball screw. The first mounting mechanism further includes a spindle mounted to the stage plate, where the spindle is configured to rotate at high speed and configured to provide steady position of a sample to be inspected, and a disk chuck mounted on the spindle, where the disk chuck is configured to clamp the sample for inspection.

The second mounting mechanism includes a vertical plate mounted to the vertical frame on a pair of vertical frame linear guides, and a vertical servo motor configured to control position of the vertical plate using a second ball screw.

The second mounting mechanism further includes a sensor block mounted on the vertical plate, where the sensor block includes an internal dark field and bright field coaxial lighting, and a camera mounted on the vertical plate, where the camera is coupled to the sensor block through an infinity optical system and an optical coupler. The infinity optical system is configured to transmit images of the sample to the camera. The optical coupler is configured to isolate the optics of the sensor block from the camera, and adjust magnifications of images of the sample.

The second mounting mechanism further includes a sensor turret configured to hold the set of sensors at predetermined positions, where the set of sensors are configured to be rotated to position for inspecting the sample while the sample remains substantially stationery. The set of sensors includes microscope objective lens configured to detect defects using microscopic imaging of the sample, piezoelectric sensors configured to detect defects using small precise movements with respect to the sample, and laser scatterometer configured to detect defects by using scattered light patterns obtained from the sample. The set of sensors further includes magnetic read and write head configured to read and write magnetic patterns on magnetic media, and mechanical scriber configured to scribe surface of the sample.

The second mounting mechanism further includes an atomic force microscope and a first corresponding camera configured to inspect the sample, wherein the first corresponding camera is mounted vertically underneath the atomic force microscope; and/or an atomic force microscope and a second corresponding camera configured to inspect the sample, wherein the second corresponding camera is mounted laterally with respect to the atomic force microscope.

In another embodiment, a method for constructing an inspection instrument includes providing a base plate and a vertical frame, where the base plate and the vertical frame are configured to provide structural support of the inspection instrument, providing a first mounting mechanism coupled to the base plate, where the first mounting mechanism is configured to hold a sample for inspection, and providing a second mounting mechanism coupled to the vertical frame, where the second mounting mechanism is configured to hold a set of sensors and an optical system for inspecting the sample. The first mounting mechanism and the second mounting mechanism are decoupled from each other to reduce impact of movements of the sample to the set of sensors and the optical system. The method of providing a base plate includes creating a first opening configured to house at least a part of the first mounting mechanism, where the first opening reduces center of gravity of the first mounting mechanism with respect to the base plate; and the first opening reduces distance between the second mounting mechanism and the vertical frame to improve stability of the inspection instrument. The method of providing a vertical frame includes creating a second opening configured to provide a clearance to install a stage plate from back of the inspection instrument.

The method of providing a first mounting mechanism includes mounting a stage plate to the base plate on a pair of base plate linear guides, and providing a stage servo motor configured to control position of the base plate using a first ball screw. The method of providing a first mounting mechanism further includes mounting a spindle to the stage plate, where the spindle is configured to rotate at high speed and configured to provide steady position of a sample to be inspected, and mounting a disk chuck on the spindle, where the disk chuck is configured to clamp the sample for inspection.

The method of providing a second mounting mechanism includes mounting a vertical plate to the vertical frame on a pair of vertical frame linear guides, and providing a vertical servo motor configured to control position of the vertical plate using a second ball screw. The method of providing a second mounting mechanism further includes mounting a sensor block on the vertical plate, where the sensor block includes internal dark field and bright field coaxial lighting, and mounting a camera on the vertical plate, where the camera is coupled to the sensor block through an infinity optical system and an optical coupler. The infinity optical system is configured to transmit images of the sample to the camera, and the optical coupler is configured to isolate the optics of the sensor block from the camera, and adjust magnifications of images of the sample.

The method of providing a second mounting mechanism further includes providing a sensor turret configured to hold the set of sensors at predetermined positions, where the set of sensors are configured to be rotated to position for inspecting the sample while the sample remains substantially stationery. The set of sensors includes microscope objective lens configured to detect defects using microscopic imaging of the sample, piezoelectric sensors configured to detect defects using small precise movements with respect to the sample, and laser scatterometer configured to detect defects by using scattered light patterns obtained from the sample. The set of sensors further includes magnetic read and write head configured to read and write magnetic patterns on magnetic media, and mechanical scriber configured to scribe surface of the sample.

BRIEF DESCRIPTION OF THE DRAWINGS

The aforementioned features and advantages of the disclosure, as well as additional features and advantages thereof, will be more clearly understandable after reading detailed descriptions of embodiments of the disclosure in conjunction with the following drawings.

FIG. 3 illustrates a bottom-view of the inspection instrument of FIG. 1 according to embodiments of the present invention.

FIG. 4 illustrates a back-view of the inspection instrument of FIG. 1 according to embodiments of the present invention.

FIG. 5a illustrates a side-view of another inspection instrument according to embodiments of the present invention.

Like numbers are used throughout the figures.

DESCRIPTION OF EMBODIMENTS

Embodiments of inspection instrument are disclosed. The following descriptions are presented to enable any person skilled in the art to make and use the disclosure. Descriptions of specific embodiments and applications are provided only as examples. Various modifications and combinations of the examples described herein will be readily apparent to those skilled in the art, and the general principles defined herein may be applied to other examples and applications without departing from the spirit and scope of the disclosure. Thus, the present disclosure is not intended to be limited to the examples described and shown, but is to be accorded the widest scope consistent with the principles and features disclosed herein.

Figure 1:
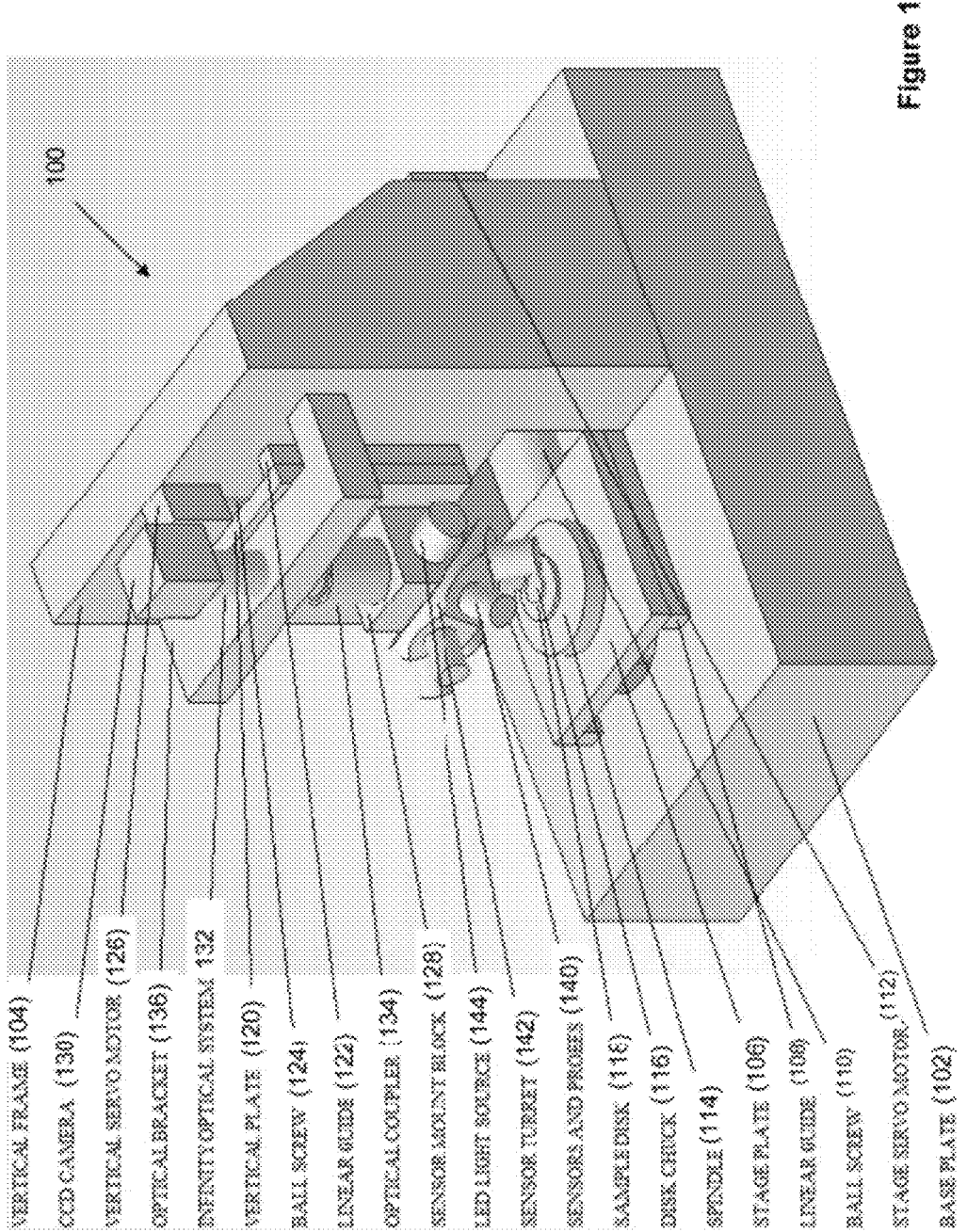
FIG. 1 illustrates a three dimensional front-view of an inspection instrument according to embodiments of the present invention.

FIG. 1 illustrates a three dimensional front-view of an inspection instrument according to one embodiment of the present invention. As shown in FIG. 1, the inspection instrument 100 includes a base plate 102 and a vertical frame 104 configured to provide structural support for stability of the inspection instrument 100. The base plate 102 and vertical frame 104 can be made of heavy materials such as granite or cast iron. The inspection instrument 100 further includes a stage plate 106 mounted to the base plate on a pair of base plate linear guides 108. The position of the stage plate 106 is controlled by a high precision ball screw 110 driven with a stage servo motor 112 or stepper motor (not shown). A spindle 114, which is capable of both high speed rotation (up to 15000 rpm) and steady positioning of samples to be inspected, is mounted on the stage plate 106. A disk chuck 116 is mounted on the spindle 114 where a sample (for example a sample disk 118) to be inspected can be clamped thereon. Persons skilled in the art can appreciate that the sample being inspected can include, but not limited to, a semiconductor wafer, an integrated circuit, and a magnetic disk.

The inspection instrument 100 further includes a vertical plate 120 mounted to the vertical frame 104 on a pair of vertical frame linear guides 122. The position of the vertical plate 120 is controlled by a high precision ball screw 124 driven with vertical servo motor 126 or stepper motor (not shown). The inspection instrument 100 further includes an inspection block 128, also referred to as the sensor mount block or the sensor block for short, with internal dark field and bright field coaxial lighting provision, such as LED light source 144, being mounted on the vertical plate 120.

A CCD camera 130 mounted on the vertical plate 120 can be coupled to the sensor block 128 through an infinity optical system 132 and an optical coupler 134. The infinity optical system is configured to transmit images of a sample to the CCD camera 130. The optical coupler 134 is configured to isolate the optics of the sensor block from the camera, and it can also be used for adjusting magnifications of images obtained from the sample. An optical bracket 136 mounted on the vertical frame 104 is used to hold the infinity optical system 132 in place. The CCD camera 130 contains tulan lens that focuses light rays from the infinity corrected objective lens (infinite or finite corrected) into sensors (not shown) of the CCD camera 130. Different types of camera may be used in place of the CCD camera 130, including but not limited to photo multiplier sensors and infrared cameras. it shall be noted that the inspection block 128 is mechanically decoupled from the CCD camera system 130 so that vibrations on the CCD camera system 130 can be bypassed to the vertical frame 104.

Various inspection, testing, analysis and measurement sensors and probes 140 can be mounted through a sensor turret 142 onto the inspection block 128. The sensor turret 142 can be configured to hold a set of sensors or probes at predetermined positions, and the set of sensors and probes can be rotated to a desired position for inspecting a sample without moving the sample. The inspection block 128 provides attachment for illumination source, such as LED light source 144, optical passage, and bright field optics. The inspection block 128 also aligns the optical system, for example, optical coupler 134 and LED light source 144, to the sensors and probes 140. In some aspects of the present invention, the optical coupler 134 separates the infinity optical system 132 from the sensor mounting block 128. In addition, the optical coupler 134 shields outside light to the optical system, and provides no mechanical contact between the infinity optical system 132 and the optical coupler 134. It shall be noted that vibration isolation can be an issue for many sensors including the AFM (atomic force microscope) sensor used in conventional testers. One of the objects, advantages and benefits of the present invention is to provide mechanisms for ensuring vibration isolation of the various components of the instrument.

The inspection, testing, analysis and measurement sensors and probes 140 may include, but not limited to: a) microscope objective lens configured to perform microscopic imaging with magnifications from 1 to 100 times, bright field or dark field imaging; b) magnetic read and write head configured to read and write magnetic patterns on magnetic media, and detect defects with the analysis of read signals; c) glide head configured with slider with piezoelectric sensor mounted on the back, and can be used for flying on smooth media at a spacing from 1 nm to more than 10 nm, and generates signals when defects are detected; d) laser scatterometer configured to detect defects by examining scattered light patterns from the sample being inspected; e) mechanical scriber configured to scribe the surface to be used as a marker. Persons skilled in the art can appreciate that other sensors in the right form factor can be designed to take advantage of the sensor turret 142.

Figure 2:
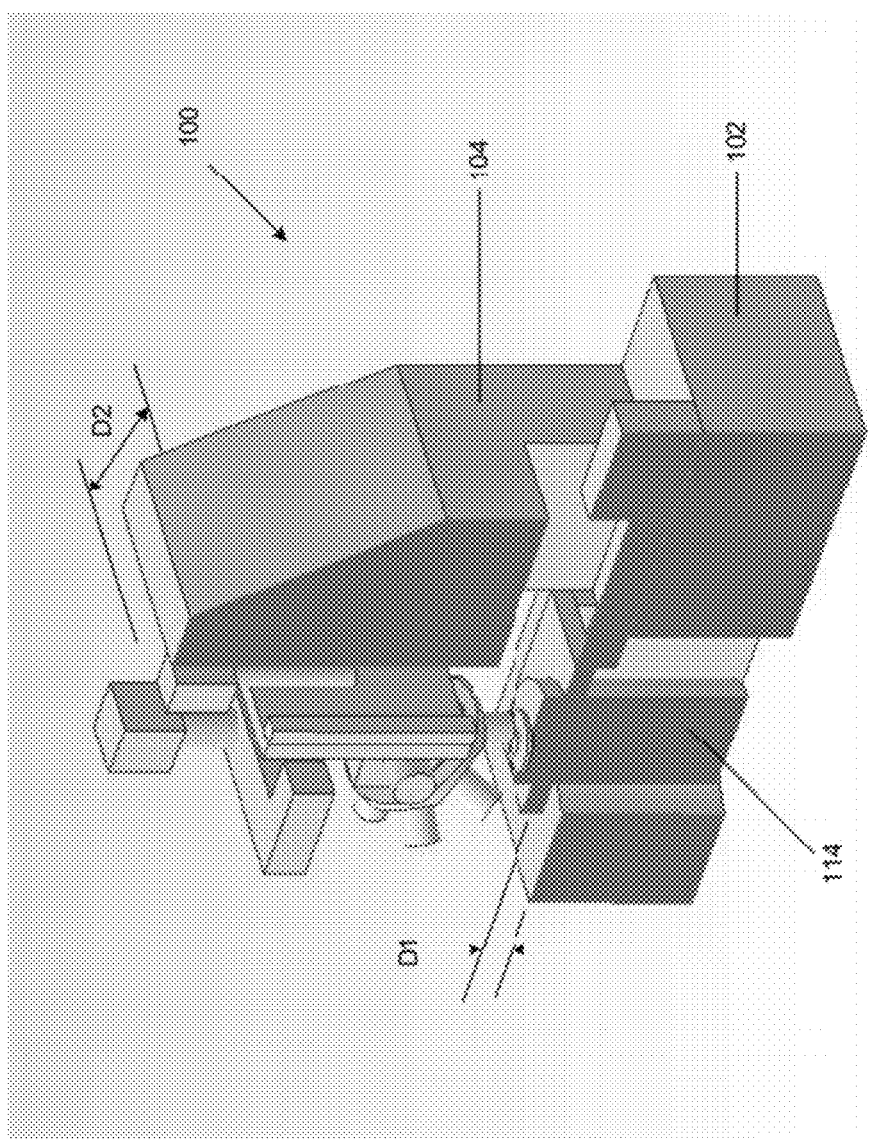
FIG. 2 illustrates a cross-sectional view of the inspection instrument of FIG. 1 according to embodiments of the present invention.

FIG. 2 illustrates a cross-sectional view of the inspection instrument of FIG. 1. As shown in the view of FIG. 2, by employing the separated base plate 102 and vertical frame 104, the inspection instrument provides a rigid space relationship between the sensors and optical system (mounted on the vertical frame 104) and the sample object being inspected (mounted on the base plate 102). An opening is provided in the base plate 102 to house the spindle 114. This arrangement reduces the distance (D1) between the sample and the base plate 102. In addition, this arrangement also reduces the distance (D2) between the optical system and the vertical frame 104. Therefore, it enhances the stability of the entire inspection instrument and produces higher quality images with the disclosed inspection instrument.

FIG. 3 illustrates a bottom-view of the inspection instrument of FIG. 1. As shown in FIG. 3, an opening 302 is provided at the base plate 102 of the inspection instrument for housing the spindle 114. As a result, the opening 302 allows the various components mounted on the base plate 102 as well as the various components mounted on the vertical frame 104 to be placed at locations having lower center of gravity. Thus, this design of the base plate 102 and the placement of the spindle 114 further promote the stability of the inspection instrument.

FIG. 4 illustrates a back-view of the inspection instrument of FIG. 1. In this example, by having an opening 402 in the vertical frame 104, it provides a clearance to install the stage plate 106 from the back of the inspection instrument. In addition, it allows another means of access to the stage plate 106.

According to aspects of the present invention, the inspection instrument is designed to increase accuracy and image quality of the object under inspection by 1) reducing vibrations through decoupling components mounted on the base plate 102 and vertical frame 104; 2) reducing impacts of vibration in the optical system by decoupling the sensors and probes 140 from the CCD camera 130 through the infinity optical system 132 and the optical coupler 134; 3) lowering center of gravity of the instrument using an opening in the base plate 102 to house the spindle 114.

FIG. 5a illustrates a side-view of another inspection instrument according to one embodiment of the present invention. The inspection instrument 500 shown in FIG. 5a shares a number of common components (as indicated by the same numbered numerals) as the inspection instrument shown in FIG. 1. In addition, the inspection instrument 500 includes an atomic force microscope (AFM) 502, a camera 504, and active vibration isolation pad 506.

According to one embodiment of the present disclosure, AFM is a high-resolution type of scanning probe microscopy, with demonstrated resolution on the order of fractions of a nanometer, more than 1000 times better than the optical diffraction limit. The AFM is a tool for imaging, measuring, and manipulating matter at the nanoscale. The information is gathered by "feeling" the surface with a mechanical probe. Piezoelectric elements that facilitate tiny but accurate and precise movements on an electronic command enable the precise scanning. In some variations, electric potentials can also be scanned using conducting cantilevers. In other implementations, currents may be passed through the tip to probe the electrical conductivity or transport of the underlying surface. In one implementation, the AFM includes of a cantilever with a sharp tip (probe) at its end that is used to scan the specimen surface. The cantilever is typically silicon or silicon nitride with a tip radius of curvature on the order of nanometers. When the tip is brought into proximity of a sample surface, forces between the tip and the sample lead to a deflection of the cantilever. Forces that are measured in AFM include mechanical contact force, capillary forces, chemical bonding, electrostatic forces, magnetic forces, etc. Along with force, additional quantities may be measured simultaneously through the use of specialized types of probe. Typically, the deflection is measured using a laser spot reflected from the top surface of the cantilever into an array of photodiodes. Other methods that are used include optical interferometry, capacitive sensing or piezoresistive AFM cantilevers. These cantilevers are fabricated with piezoresistive elements that act as a strain gauge. Using a Wheatstone bridge, strain in the AFM cantilever due to deflection can be measured.

If the tip was scanned at a constant height, a risk may exist that the tip collides with the surface, causing damage to the sample. Hence, in most cases a feedback mechanism is employed to adjust the tip-to-sample distance to maintain a constant force between the tip and the sample. Traditionally, the sample is mounted on a piezoelectric tube that can move the sample in the z direction for maintaining a constant force, and the x and y directions for scanning the sample. Alternatively a 'tripod' configuration of three piezo crystals may be employed, with each responsible for scanning in the x, y and z directions. This eliminates some of the distortion effects seen with a tube scanner. In newer designs, the tip is mounted on a vertical piezo scanner while the sample is being scanned in X and Y using another piezo block. The resulting map of the area z=f(x,y) represents the topography of the sample.

According to one embodiment of the present disclosure, the AFM can be operated in a number of modes, depending on the application. In general, possible imaging modes are divided into static (also called contact) modes and a variety of dynamic (or non-contact) modes where the cantilever is vibrated. When the inspection instrument 500 is operated under one of the AFM modes, the sample 118 is moved under the AFM for inspection. Note that the AFM scanner is recessed behind the sensor turret 142 and the other sensor(s) 140; the camera 504 is used to observe the AFM tip to enable the operator to make changes on it when necessary. Alternatively, when the inspection instrument 500 is operated under one of the sensor modes, the sample 118 is moved under a sensor 140 for inspection, such as scribe, glide, or optical inspection.

Figure 5B:
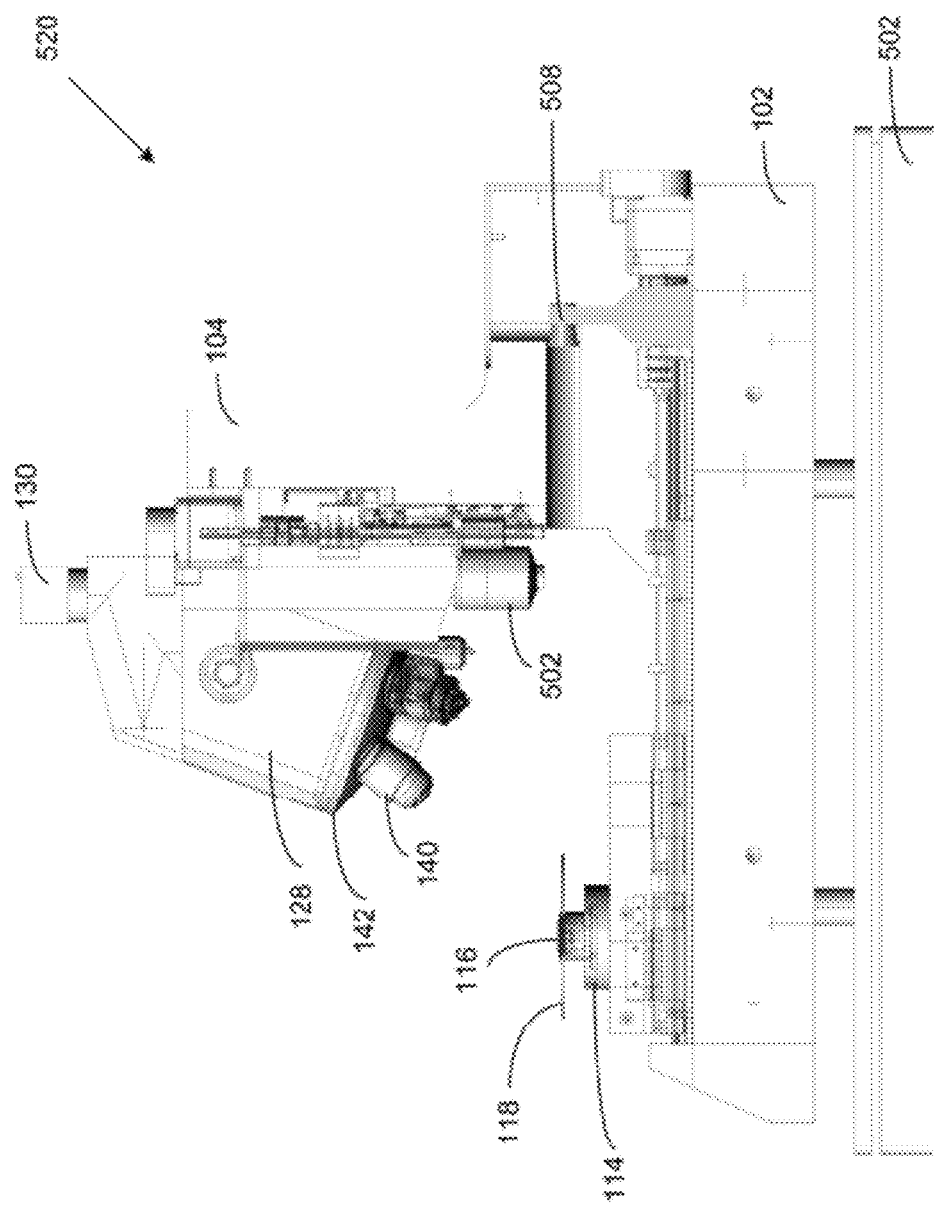
FIG. 5b illustrates a side-view of yet another inspection instrument according to embodiments of the present invention.

FIG. 5b illustrates a side-view of yet another inspection instrument according to embodiments of the present invention. The inspection instrument 520 shown in FIG. 5b is similar to the inspection instrument shown in FIG. 5a as many components are substantially the same. One of the differences between FIG. 5a and FIG. 5b is that the inspection instrument 520 includes a lateral camera 508 instead of camera 504 located at the bottom of the inspection instrument 500.

Similar to the inspection instrument 500 shown in FIG. 5a, when the inspection instrument 520 is operated in one of the AFM modes, the sample 118 is placed under the AFM for inspection. It shall be noted that the AFM scanner is recessed behind the sensor turret 142 and the other sensor(s) 140, where the camera 508 is used to observe the AFM tip to enable the operator to make changes on it when necessary. In other implementations, both camera 504 and camera 508 may be installed and configured to observe the AFM tip. Alternatively, when the inspection instrument 520 is operated under one of the sensor modes, the sample 118 is placed under a sensor 140 for inspection, such as scribe, glide, or optical inspection.

According to aspects of the present invention, the inspection instrument is designed to use multiple sensors to inspect a sample without moving the physical location of the sample. The multiple sensors may be selected to complement each other such that any defect on the sample may be correlated and examined with complimentary methods on the same inspection instrument without loss of coordinates. Therefore, the disclosed inspection instrument can increase test throughput as the sample stays at the same location for a full course of analysis and inspections. With the arrangement of multiple sensors, the present invention enables a coherent use of analysis sensors and searching sensors in combination. The method can perform analysis with certain analysis sensors for defects or features on a sample, and then the method is combined with other kind of searching sensors for searching similar defects or features on the sample. In this way, the methodology addresses the issue that certain analysis sensors may not be capable of searching for defects or features because of their limited field-of-view. For example, a glide is great with searching for defect locations, but its AFM has only 100 um×100 um maximum scanning area. So it will be challenging, without special technique, to relocate the defect after the defect is found by the glide when the sample is moved from the glide tester to the AFM with conventional inspection instruments. With the present invention, different analysis sensors and searching sensors can be brought to use with the sensor turret and without moving the sample under inspection.

One skilled in the relevant art will recognize that many possible modifications and combinations of the disclosed embodiments may be used, while still employing the same basic underlying mechanisms and methodologies. The foregoing description, for purposes of explanation, has been written with references to specific embodiments. However, the illustrative discussions above are not intended to be exhaustive or to limit the disclosure to the precise forms disclosed. Many modifications and variations are possible in view of the above teachings. The embodiments were chosen and described to explain the principles of the disclosure and their practical applications, and to enable others skilled in the art to best utilize the disclosure and various embodiments with various modifications as suited to the particular use contemplated.

What is claimed is:

1. An inspection instrument, comprising:
a base plate and a vertical frame, the base plate and the vertical frame providing a structural support of the inspection instrument, wherein the base plate includes an opening provided for a spindle to go through, the spindle is caused to rotate at high speed and to position steadily a sample to be inspected in the inspection instrument;
a first mounting mechanism, coupled to the base plate, provided to hold the sample stationary for inspection;
an optical system;
a sensor turret provided to hold a plurality of sensors having different characteristics, provided to sense different defects on the sample, wherein the sensor turret is caused to rotate the sensors;
a second mounting mechanism, coupled to the vertical frame, provided to hold the sensor turret so as to support the sensors and the optical system, wherein the sensors are sequentially rotated with the sensor turret to take turns for inspecting the sample for one of the different defects, images of the different defects are captured through the optical system by a camera mounted on a vertical plate slidable on a pair of linear guides,
wherein the first mounting mechanism and the second mounting mechanism are decoupled from each other to reduce an impact of movements of the sample to the set of sensors and the optical system.

2. The inspection instrument of claim 1, further comprising:
a stage plate mounted movably on a pair of base plate linear guides that are mounted to the base plate, wherein a position of the stage plate is controlled by a high precision ball screw driven by a motor, wherein the vertical plate is mounted movably on a pair of vertical frame linear guides that are mounted to the vertical frame, wherein a position of the vertical plate is controlled by a high precision ball screw driven by a motor.

3. The inspection instrument of claim 2, further comprising: a disk chuck mounted on the spindle, wherein the sensor turret is caused to rotate the sensors sequentially without moving the sample being placed on the disk chuck.

4. The inspection instrument of claim 1, wherein the first mounting mechanism further comprises:
   a stage plate mounted to the base plate on a pair of base plate linear guides; and
   a stage servo motor configured to control a position of the base plate using a first ball screw.

5. The inspection instrument of claim 1, wherein the second mounting mechanism comprises:
   a vertical plate mounted to the vertical frame on a pair of vertical frame linear guides; and
   a vertical servo motor configured to control position of the vertical plate using a second ball screw.

6. The inspection instrument of claim 5, wherein the second mounting mechanism further comprises:
   a sensor block mounted on the vertical plate, wherein the sensor block includes an internal dark field and a bright field coaxial lighting, wherein the camera is coupled to the sensor block through an infinity optical system and an optical coupler, and the infinity optical system is configured to transmit images of the sample to the camera.

7. The inspection instrument of claim 6, wherein the opening on the base plate provided for the spindle to go through reduces a distance between the sample and the base plate, and also reduces a distance between the optical system and the vertical frame.

8. The inspection instrument of claim 6, wherein the optical coupler is configured to isolate the optics of the sensor block from the camera, and adjust magnifications of images of the sample.

9. The inspection instrument of claim 5, wherein the second mounting mechanism further comprises: an atomic force microscope and a first corresponding camera configured to inspect the sample, wherein the first corresponding camera is mounted vertically underneath the atomic force microscope.

10. The inspection instrument of claim 5, wherein the second mounting mechanism further comprises: an atomic force microscope and a second corresponding camera configured to inspect the sample, wherein the second corresponding camera is mounted laterally with respect to the atomic force microscope.

11. The inspection instrument of claim 1, further comprising:
    a stage servo motor provided to control a position of the base plate; and
    a vertical servo motor provided to control a position of the vertical plate.

12. The inspection instrument of claim 1, wherein the set of sensors comprise:
    a microscope objective lens configured to detect defects using microscopic imaging of the sample;
    a set of piezoelectric sensors configured to detect defects using small precise movements with respect to the sample; or
    a laser scatterometer configured to detect defects by using scattered light patterns obtained from the sample.

13. The inspection instrument of claim 12, wherein the set of sensors further comprises:
    a magnetic read and write head configured to read and write magnetic patterns on magnetic media; and
    a mechanical scriber configured to scribe surface of the sample.

14. The inspection instrument of claim 1, wherein the defects are captured in the images via a microscopic lens so that the images can be correlatively analyzed.

15. A method for constructing an inspection instrument, comprising:
    providing a base plate and a vertical frame for a structural support of the inspection instrument, wherein the base plate includes an opening provided for a spindle to go through, the spindle is configured to rotate at high speed and to position steadily a sample to be inspected in the inspection instrument, wherein the spindle is provided to hold a sample on a disk chuck;
    providing a first mounting mechanism, coupled to the base plate, to hold the sample for inspection;
    providing a second mounting mechanism, coupled to the vertical frame, to support a sensor turret mounted with a set of sensors and an optical system for inspecting the sample, each of the sensors having different characteristics provided to detect different defects on the sample, wherein the sensor turret is caused to rotate the sensors sequentially for inspecting the sample for the different defects; and
    capturing images of the different defects by the sensors via the same optical system mounted on a vertical plate slidable on a pair of linear guides,
    wherein the first mounting mechanism and the second mounting mechanism are decoupled from each other to reduce impact of movements of the sample to the set of sensors and the optical system.

16. The method of claim 15, further comprising:
    providing a stage plate mounted movably on a pair of base plate linear guides that are mounted to the base plate, wherein a position of the stage plate is controlled by a high precision ball screw driven by a motor; and
    providing the vertical plate mounted movably on a pair of vertical frame linear guides that are mounted to the vertical frame, wherein a position of the vertical plate is controlled by a high precision ball screw driven by a motor.

17. The method of claim 16, wherein the sensor turret causes the sensors sequentially rotated without moving the sample being placed on a disk chuck mounted on the spindle.

18. The method of claim 15, wherein providing a first mounting mechanism further comprises:
    providing a stage plate mounted to the base plate on a pair of base plate linear guides; and
    providing a stage servo motor configured to control a position of the base plate using a first ball screw.

19. The method of claim 15, wherein said providing a second mounting mechanism comprises:
    mounting a vertical plate to the vertical frame on a pair of vertical frame linear guides; and
    providing a vertical servo motor configured to control position of the vertical plate using a second ball screw.

20. The method of claim 19, wherein said providing a second mounting mechanism further comprises:
    mounting a sensor block on the vertical plate, wherein the sensor block includes internal dark field and bright field coaxial lighting; and
    mounting a camera on the vertical plate, wherein the camera is coupled to the sensor block through an infinity optical system and an optical coupler.

21. The method of claim 20, wherein the infinity optical system is configured to transmit images of the sample to the camera.

22. The method of claim 20, wherein the optical coupler is configured to isolate the optics of the sensor block from the camera, and adjust magnifications of images of the sample.

23. The method of claim 19, wherein said providing a second mounting mechanism further comprises:
providing a sensor turret configured to hold the set of sensors at predetermined positions, wherein the set of sensors are configured to be rotated to a position for inspecting the sample while the sample remains substantially stationary.

24. The method of claim 23, wherein the set of sensors comprises:
a microscope objective lens configured to detect defects using microscopic imaging of the sample;
a set of piezoelectric sensors configured to detect defects using small precise movements with respect to the sample; or
a laser scatterometer configured to detect defects by using scattered light patterns obtained from the sample.

25. The method of claim 24, wherein the set of sensors further comprise:
a magnetic read and write head configured to read and write magnetic patterns on magnetic media; and
a mechanical scriber configured to scribe surface of the sample.

26. The method of claim 19, wherein the second mounting mechanism further comprises:
an atomic force microscope and a first corresponding camera configured to inspect the sample, wherein the first corresponding camera is mounted vertically underneath the atomic force microscope.

27. The method of claim 19, wherein the second mounting mechanism further comprises:
an atomic force microscope and a second corresponding camera configured to inspect the sample, wherein the second corresponding camera is mounted laterally with respect to the atomic force microscope.

28. The method of claim 15, wherein said providing a vertical frame comprises: creating a second opening configured to provide a clearance to install a stage plate from back of the inspection instrument.

\* \* \* \* \*